United States Patent [19]

Kordes et al.

[11] Patent Number: Plant 5,575

[45] Date of Patent: Oct. 22, 1985

[54] ROSE PLANT KORFLUG

[75] Inventors: Reimer Kordes; Werner Kordes; Hermann Kordes, all of Sparrieshoop, Fed. Rep. of Germany

[73] Assignee: Jackson & Perkins Company, Medford, Oreg.

[21] Appl. No.: 554,887

[22] Filed: Nov. 25, 1983

[51] Int. Cl.[4] ..... A01H 5/00

[52] U.S. Cl. ..... Plt./18

[58] Field of Search ..... Plt./18

*Primary Examiner*—James R. Feyrer

*Attorney, Agent, or Firm*—Klarquist, Sparkman, Campbell, Leigh & Whinston

[57] ABSTRACT

A new hybrid tea rose with large, long lasting flowers having pink petals of unusual thickness. The rose is suitable for greenhouse production, presenting buds of cutting size on medium length stems.

1 Drawing Figure

This present invention relates to a new and distinct variety of rose plant of the hybrid tea class which was originated by us by crossing an unnamed variety with the variety Lady Like, non-patented.

The primary objective of this breeding was to produce a new rose variety suitable for greenhouse cut flower production in the pink color range. This objective was substantially achieved along with other desirable improvements as evidenced by the following unique combination of characteristics which are outstanding in the new variety and which distinguish it from its parents, as well as from all other varieties of which we are aware:

1. Light pink bud and open flower.
2. Unusually stiff, firm petals, approximately 25 per flower.
3. Production of a suitable quantity of medium length stems under greenhouse conditions.
4. Resistance to mildew.
5. Little or no fragrance.

Asexual reproduction of this new variety by budding, as performed at Irvine and Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Lady Like.

Classification:

*Botanical.*—Rosa hybrid.

*Commercial.*—Hybrid tea.

FLOWER

Observations made from specimens grown in a greenhouse at Irvine, Calif. in August.

Blooming habit: Continuous.

Bud:

*Size.*—$1\frac{1}{8}''$ when petals start to unfurl.

*Form.*—Pointed ovoid.

*Color.*—When sepals first divide, blend of pink to near white, darkest edges near Red Group 50B through 49A and B to 49C and D. When half blown; upper side of petals near 49A; lower side of petals near 49B.

*Sepals.*—Color: Outer surface slightly pubescent, Green 138B. Three appendaged sepals lightly appendaged. Two unappendaged sepals hairy edged.

*Receptacle.*—Color: Green 138B. Shape: Funnel. Size: Large. Surface: Nearly smooth with very few hairs.

*Peduncle.*—Length: Long. Surface: Glandular. Color: Light green. Strength: Stiff, erect.

*Opening.*—Spiral fashion.

Bloom:

*Size.*—Medium. Average open size: 4 to $4\frac{1}{2}''$.

*Borne.*—Mostly singly.

*Stems.*—Medium, strong.

*Form.*—When first open, cupped. Permanence: Flattens, outer petal edges slightly curled.

*Petalage.*—Number of petals under normal conditions: approximately 25.

*Color.*—Center of flower: Upper side of petals blend of Red Group 49A and 49B; reverse side of petals 49A and 49B; base of petals exhibit yellow overtones. General tonality from a distance, Pink-Red Group 49B.

*Variegations.*—Occasionally some green pigment in outer petals.

*Discoloration.*—General tonality at end of first day: Pink, Red Group 49B. Third day: Pink, Red Group 49C.

*Fragrance.*—None.

Petals:

*Texture.*—Thick, very stiff petals.

*Shape.*—Round.

*Form.*—Tips slightly recurved.

*Arrangement.*—Imbricated. Petaloids in center, few.

*Persistence.*—Drop off cleanly.

*Lastingness.*—On the plant, very long. As cut flower, very long.

Reproductive parts:

*Anthers.*—Medium. Color: Yellow. Arrangement: Regular around styles.

*Filaments.*—Color: Reddish.

PLANT

Form: Bush.

Growth: Vigorous, upright, branching.

Foliage: Number of leaflets on normal mid-stem leaves: 5, occasionally 7.

*Size.*—Medium.

*Quantity.*—Normal.

*Color.*—New foliage: Greyed Purple 187C. Old foliage: Green 139A.

Leaflets:

*Shape.*—Oval pointed.

*Texture.*—Leathery, flat on upper side.

*Edge.*—Serrated.

*Serration.*—Single, small.

*Petiole.*—Rachis: Color: Green to reddish. Underside: Prickles.

*Stipules.*—Medium, bearded.

*Disease resistance.*—Resistant to mildew under normal growing conditions at Irvine, Calif.

Wood:

*New wood.*—Color: Reddish. Bark: Smooth.

*Old wood.*—Color: Green. Bark: Smooth.

Prickles:

*Quantity.*—On main stalks from base: ordinary. On laterals from stalk; ordinary.

*Form.*—Medium, slightly hooked downward.

*Color when young.*—Brown.

*Position.*—Irregular.

Small prickles:

*Quantity.*—On main stalks, few. On laterals, few.

*Color.*—Brown.

We claim:

1. A new and distinct variety of rose plant of the hybrid tea class, substantially as herein shown and described, characterized particularly as to novelty by the unique combination of its production of cuttable buds on medium length stems, the buds being of a light pink color with very stiff petals.

* * * * *

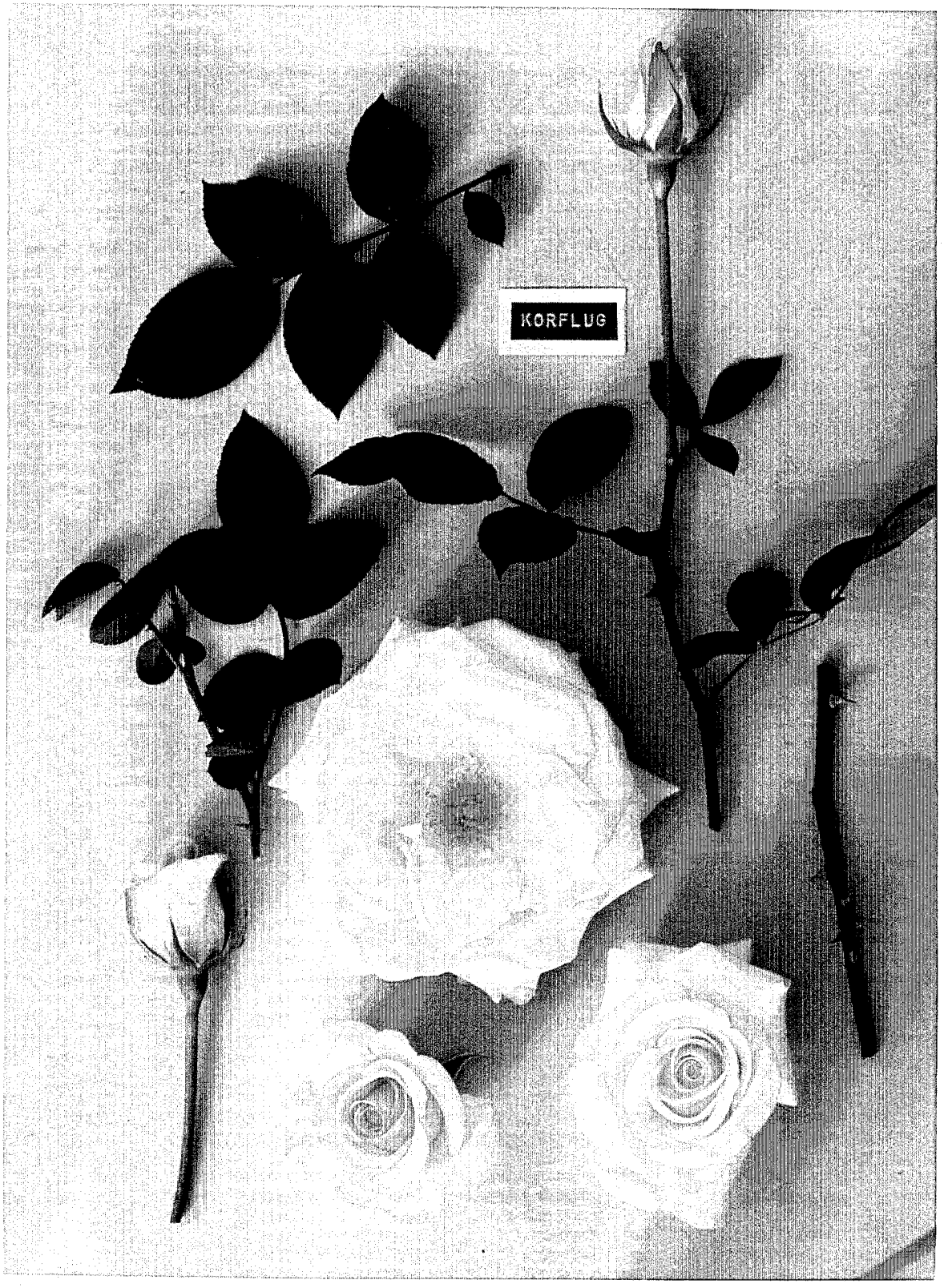
KORFLUG